United States Patent
Wittkampf et al.

(10) Patent No.: US 12,383,331 B2
(45) Date of Patent: Aug. 12, 2025

(54) SYSTEMS AND METHODS FOR LIMITING ARCING IN ELECTROPORATION SYSTEMS

(71) Applicant: St. Jude Medical, Cardiology Division, Inc., St. Paul, MN (US)

(72) Inventors: Frederik Henricus Matheus Wittkampf, Lage Vuursche (NL); René Van Es, Utrecht (NL); Israel Byrd, Richfield, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 915 days.

(21) Appl. No.: 16/977,590

(22) PCT Filed: Mar. 5, 2019

(86) PCT No.: PCT/US2019/020711
§ 371 (c)(1),
(2) Date: Sep. 2, 2020

(87) PCT Pub. No.: WO2019/173309
PCT Pub. Date: Sep. 12, 2019

(65) Prior Publication Data
US 2020/0405387 A1    Dec. 31, 2020

Related U.S. Application Data

(60) Provisional application No. 62/639,151, filed on Mar. 6, 2018.

(51) Int. Cl.
| | | |
|---|---|---|
| A61B 18/14 | (2006.01) | |
| A61B 5/287 | (2021.01) | |
| A61B 18/00 | (2006.01) | |
| A61B 18/12 | (2006.01) | |

(Continued)

(52) U.S. Cl.
CPC .......... *A61B 18/1492* (2013.01); *A61B 5/287* (2021.01); *A61B 2018/00398* (2013.01);
(Continued)

(58) Field of Classification Search
CPC ............... A61B 18/1492; A61B 5/287; A61B 2018/00398; A61B 2018/00613;
(Continued)

(56) References Cited

U.S. PATENT DOCUMENTS

| | | |
|---|---|---|
| 5,549,646 A | 8/1996 | Katz et al. |
| 9,283,051 B2 | 3/2016 | Garcia et al. |

(Continued)

FOREIGN PATENT DOCUMENTS

| | | |
|---|---|---|
| WO | 2007035537 A2 | 3/2007 |
| WO | 2018102376 A1 | 6/2018 |

OTHER PUBLICATIONS

International Search Report for PCT/US2019/020711, dated Jun. 3, 2019, 5pps.

*Primary Examiner* — Khadijeh A Vahdat
*Assistant Examiner* — Abigail M Ziegler
(74) *Attorney, Agent, or Firm* — Armstrong Teasdale LLP

(57) ABSTRACT

The present disclosure provides methods and systems for limiting arcing during an electroporation procedure. A method includes delivering a calibration shock using a catheter, measuring a current delivered during the calibration shock and a voltage delivered during the calibration shock, calculating, using a processing device, a calibration shock impedance based on the delivered current and the delivered voltage, calculating, using the processing device, a bridge impedance based on the calibration shock impedance and a target impedance, wherein the bridge impedance is a difference between the calibration shock impedance and the target impedance, adding an impedance in series with the catheter, the impedance being greater than or equal to the bridge impedance, and delivering a therapeutic shock using the catheter in series with the added impedance.

16 Claims, 6 Drawing Sheets

(51) Int. Cl.
 *A61B 18/16* (2006.01)
 *A61B 34/20* (2016.01)
 *A61N 1/39* (2006.01)
(52) U.S. Cl.
 CPC ............... *A61B 2018/00613* (2013.01); *A61B 2018/00702* (2013.01); *A61B 2018/00755* (2013.01); *A61B 2018/00791* (2013.01); *A61B 2018/00827* (2013.01); *A61B 2018/00875* (2013.01); *A61B 2018/00892* (2013.01); *A61B 2018/1266* (2013.01); *A61B 2018/167* (2013.01)
(58) Field of Classification Search
 CPC ........... A61B 2018/00755; A61B 2018/00791; A61B 2018/00827; A61B 2018/1266; A61B 2018/167; A61B 2018/00357; A61B 2018/00642; A61B 2018/00702; A61B 2018/00839; A61B 2018/00875; A61B 2018/00892; A61N 1/39
 See application file for complete search history.

(56) References Cited

U.S. PATENT DOCUMENTS

| | | | |
|---|---|---|---|
| 10,080,602 B2 | 9/2018 | Wittkampf | |
| 10,238,447 B2 | 3/2019 | Neal et al. | |
| 10,470,822 B2 | 11/2019 | Garcia et al. | |
| 2002/0029068 A1 | 3/2002 | Lyster et al. | |
| 2006/0241526 A1* | 10/2006 | Lanski | A61B 17/22004 601/2 |
| 2007/0250052 A1* | 10/2007 | Wham | A61B 18/1206 606/34 |
| 2013/0338467 A1* | 12/2013 | Grasse | A61B 18/1492 606/41 |
| 2015/0105701 A1* | 4/2015 | Mayer | A61N 7/02 601/3 |
| 2016/0287136 A1* | 10/2016 | Condie | A61B 5/6869 |
| 2016/0331441 A1 | 11/2016 | Konings | |
| 2017/0172654 A1 | 6/2017 | Wittkampf et al. | |
| 2018/0071014 A1* | 3/2018 | Neal | A61M 25/00 |

* cited by examiner

SYSTEMS AND METHODS FOR LIMITING ARCING IN ELECTROPORATION SYSTEMS

CROSS REFERENCE TO RELATED APPLICATIONS

This application is a national stage entry of PCT/US2019/020711, filed Mar. 5, 2019, which claims priority to provisional application Ser. No. 62/639,151, filed Mar. 6, 2018, which are both incorporated herein by reference in their entirety.

FIELD OF THE DISCLOSURE

The present disclosure relates generally to medical devices that are used in the human body. In particular, in many embodiments, the present disclosure relates to electroporation systems and methods of controlling electroporation systems to limit electroporation arcs from catheters.

BACKGROUND

It is generally known that ablation therapy may be used to treat various conditions afflicting the human anatomy. One such condition in which ablation therapy may be used is the treatment of atrial arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric-field induced pore formation on the cell membrane. The electric field may be induced by applying a direct current (DC) signal delivered as a relatively short duration pulse which may last, for instance, from a nanosecond to several milliseconds. Such a pulse may be repeated to form a pulse train. When such an electric field is applied to tissue in an in vivo setting, the cells in the tissue are subjected to a trans-membrane potential, which opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation.

BRIEF SUMMARY OF THE DISCLOSURE

The present disclosure generally relates to electroporation systems, and methods of controlling electroporation systems. In many embodiments, the electroporation system includes a monophasic direct current (DC) energy source connected to a catheter including several catheter electrodes. Other embodiments and descriptions of the present disclosure are set forth below.

In one embodiment, the present disclosure is directed to a method for limiting arcing during an electroporation procedure. The method includes delivering a calibration shock using a catheter, measuring a current delivered during the calibration shock and a voltage delivered during the calibration shock, calculating, using a processing device, a calibration shock impedance based on the delivered current and the delivered voltage, calculating, using the processing device, a bridge impedance based on the calibration shock impedance and a target impedance, wherein the bridge impedance is a difference between the calibration shock impedance and the target impedance, adding an impedance in series with the catheter, the impedance being greater than or equal to the bridge impedance, and delivering a therapeutic shock using the catheter in series with the added impedance.

In another embodiment, the present disclosure is directed to a system for limiting arcing during an electroporation procedure. The system includes a catheter configured to deliver a calibration shock and a therapeutic shock, and a processing device communicatively coupled to the catheter. The processing device is configured to calculate, based on a measured current delivered during the calibration shock and a measured voltage delivered during the calibration shock, a calibration shock impedance, calculate a bridge impedance based on the calibration shock impedance and a target impedance, wherein the bridge impedance is a difference between the calibration shock impedance and the target impedance, and add, prior to delivery of the therapeutic shock, an impedance in series with the catheter, the impedance being greater than or equal to the bridge impedance.

In yet another embodiment, the present disclosure is directed to a method for limiting arcing during an electroporation procedure. The method includes delivering a calibration shock using a catheter, measuring a current delivered during the calibration shock and a voltage delivered during the calibration shock, modifying, based on the current and voltage delivered during the calibration shock, a total therapeutic shock energy by one of i) adding a resistor in series with the catheter, ii) modifying a capacitance in series with the catheter, and iii) modifying a charging voltage for the capacitance in series with the catheter.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. In particular, in many embodiments, the present disclosure relates to electroporation systems and methods of controlling electroporation systems to limit electroporation arcs from catheters. In some embodiments, the catheters are intracardiac catheters. Electroporation arcs can occur from catheter electrodes to a blood pool when an insulating layer of gas covers the catheter electrode. The insulating layer of gas may be created by the electrical pulse output by an electroporation generator and the volume of gas is proportional to the energy of the amount of charge delivered. The disclosed embodiments may lead to more consistent and improved patient outcomes with less chance of undesired electrical arcing. It is contemplated, however, that the described features and methods of the present disclosure as described herein may be incorporated into any number of systems as would be appreciated by one of ordinary skill in the art based on the disclosure herein.

Figure 1:
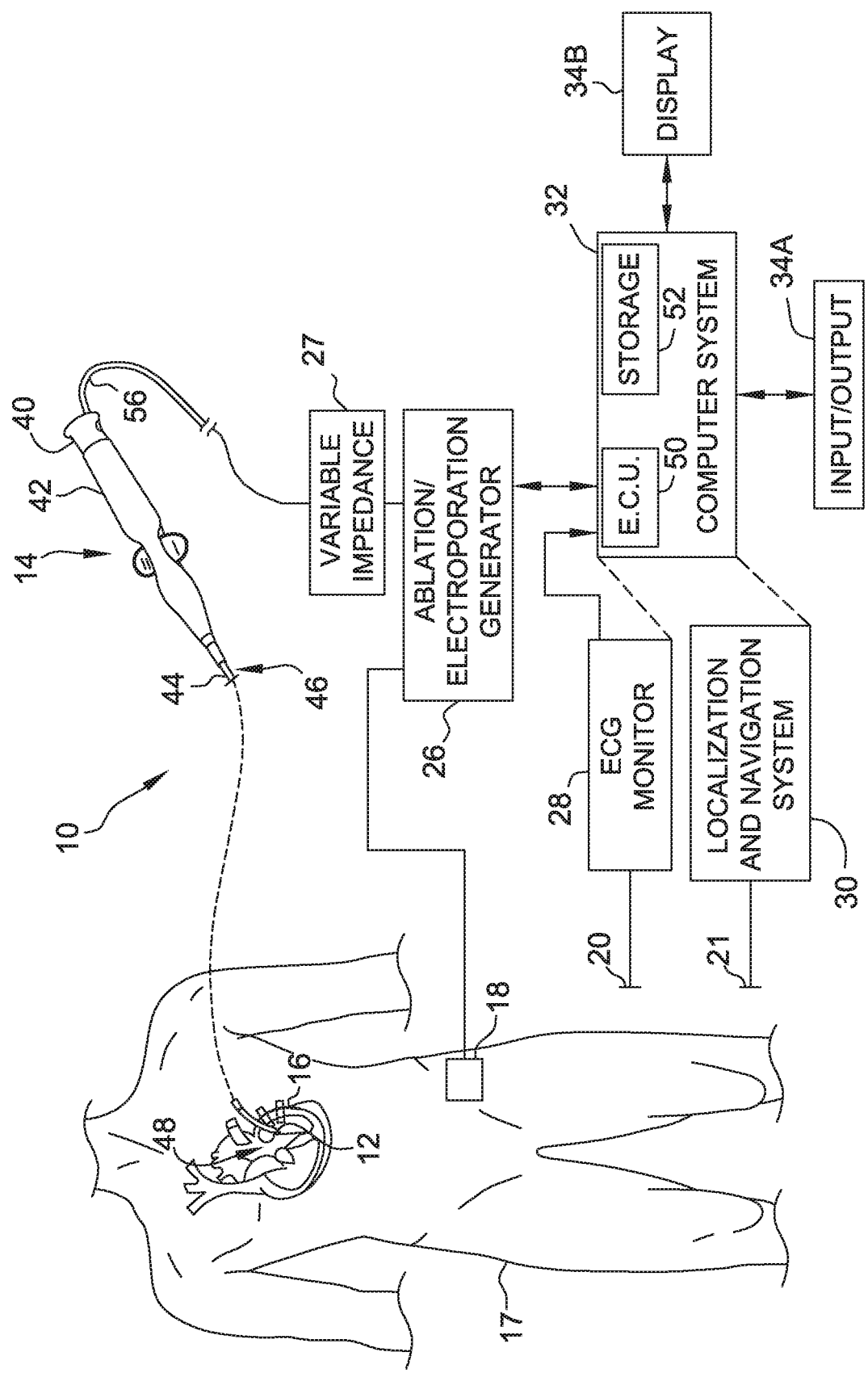
FIG. 1 is a schematic and block diagram view of a system incorporating embodiments for electroporation therapy.

Referring now to the drawings, FIG. 1 is a diagrammatic and block diagram view of a system 10 for electroporation therapy. In general, the various embodiments include an electrode assembly disposed at the distal end of a catheter. As used herein, "proximal" refers to a direction toward the end of the catheter near the clinician and "distal" refers to a direction away from the clinician and (generally) inside the body of a patient. The electrode assembly includes one or more individual, electrically-isolated electrode elements. Each electrode element, also referred to herein as a catheter electrode, is individually wired such that it can be selectively paired or combined with any other electrode element to act as a bipolar or a multi-polar electrode.

System 10 may be used for irreversible electroporation to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration direct current (DC) pulses (e.g., 0.1 to 20 ms duration) between closely spaced electrodes capable of delivering an electric field strength of about 0.1 to 1.0 kV/cm. As described in greater detail below, system 10 may be used with a high output hoop catheter for high output (e.g., high voltage and/or high current) electroporation procedures.

In one embodiment, all electrodes of the hoop catheter deliver an electric current simultaneously. That is, the electrodes are electrically connected in parallel during the application. Delivering electric current simultaneously using a plurality of electrodes arranged in a circular fashion facilitates creating a sufficiently deep lesion for electroporation. To facilitate activating electrodes simultaneously, the electrodes may be switchable between being connected to a 3D mapping system and being connected to EP amplifiers.

When using a circular hoop catheter, the current density in surrounding tissue decays linearly with distance from the electrodes when all electrodes deliver an electric current simultaneously. If, however, less than all the electrodes deliver an electric current simultaneously, the current density near electrodes that do not participate in current delivery will decay exponentially, instead of linearly. The exponential decay in current may result in insufficient lesion depth, gaps in an ablation line, and undesired procedural outcomes. Accordingly, in at least some of the embodiments described herein, current is delivered simultaneously by all electrodes (e.g., even those with low or no tissue contact). Simultaneous delivery of all electrodes in a circular arrangement may also be used for other types of electrical energy. For example, for RF ablation, simultaneous delivery (i.e., with an in-phase electrical RF current) via all electrodes (instead of a phased array or sequential delivery) may result in improved outcomes.

Figure 2:
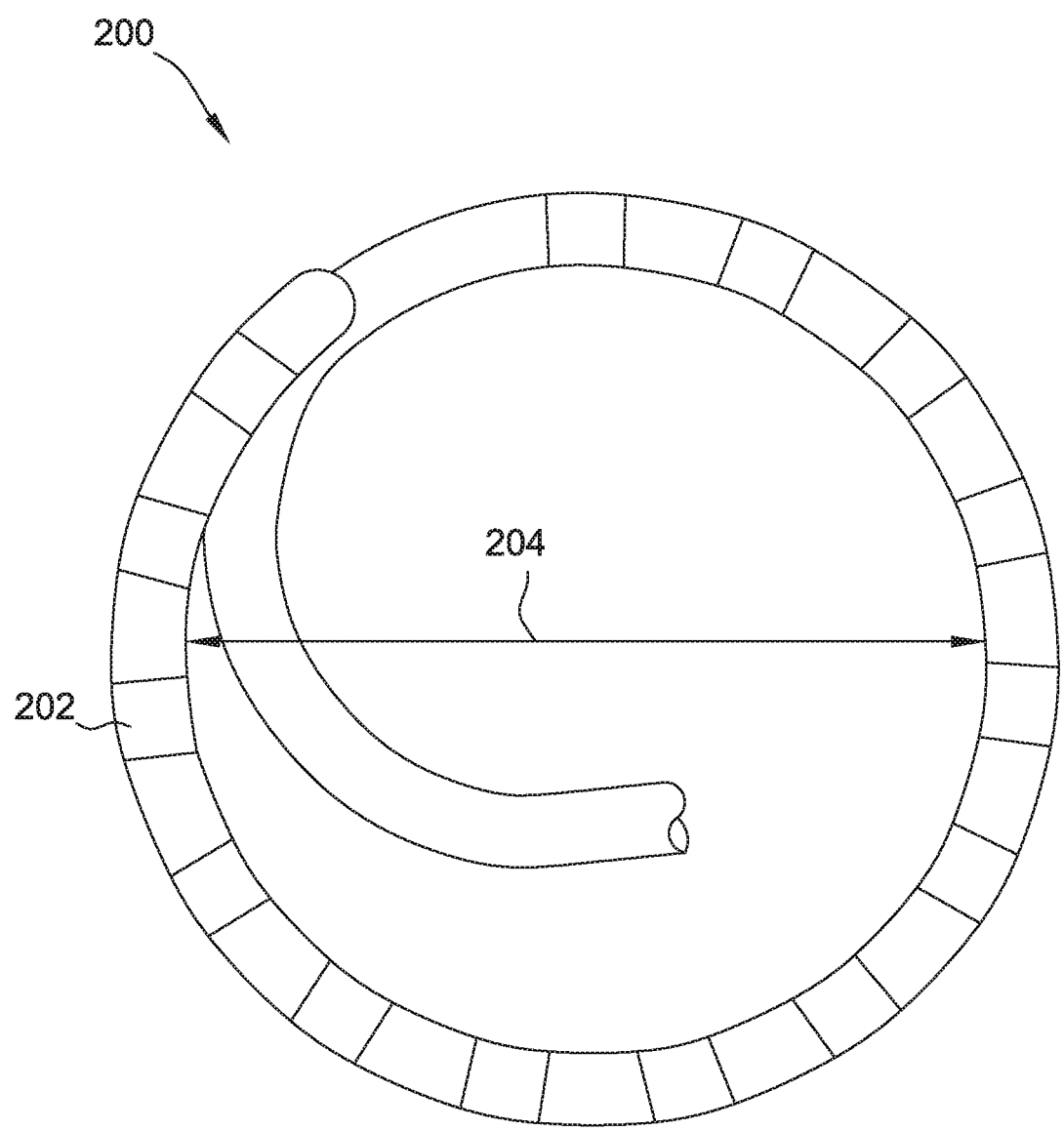
FIG. 2 is a variable diameter hoop catheter in an expanded configuration.
Figure 3:
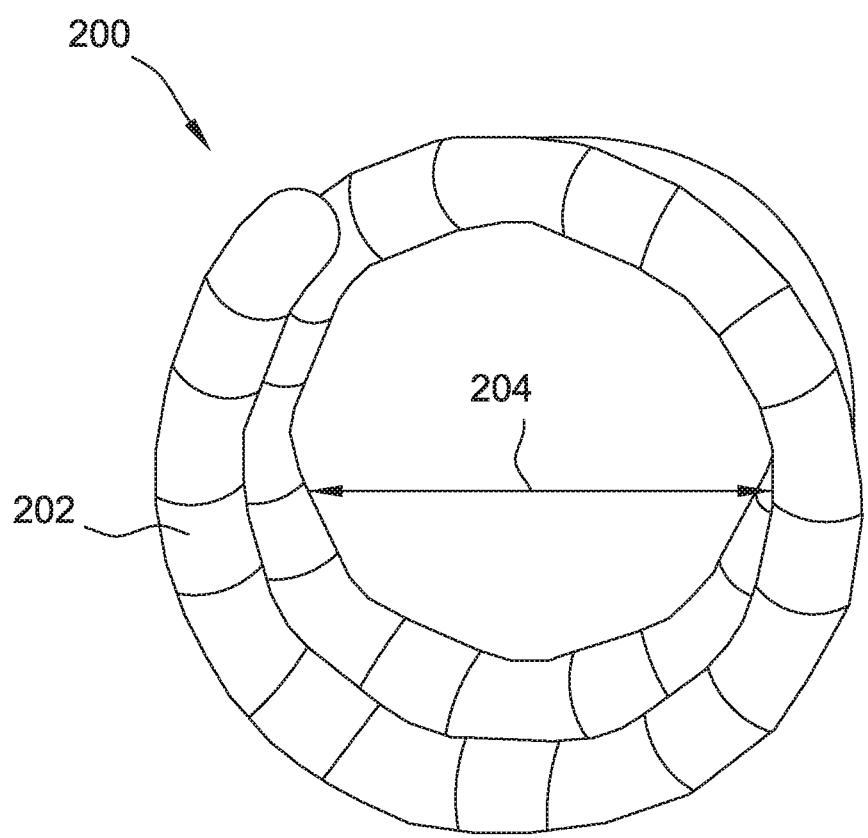
FIG. 3 is the variable diameter hoop catheter of FIG. 2 in a contracted configuration.

For a hoop catheter (e.g., as shown in FIGS. 2 and 3), when the hoop diameter is minimized, multiple electrodes will overlap, such that a subset of the electrodes form a circle by themselves (see, e.g., FIG. 3). Accordingly, in such a configuration, current can be simultaneously delivered using the subset of the electrodes without using the remaining electrodes, as the remaining electrodes overlap the subset of electrodes. In such an embodiment, determining which electrodes to use may be accomplished by determining which electrodes have the best tissue contact. By using less than all electrodes, the total energy delivered by the hoop catheter is reduced. When less than all electrodes are used, the output current may be suitable limited (e.g., by lowering energy settings and/or adding a serial resistance).

Irreversible electroporation through a multi-electrode hoop catheter may enable pulmonary vein isolation in as few as one shock per vein, which may produce much shorter procedure times compared to sequentially positioning a radiofrequency (RF) ablation tip around a vein.

It should be understood that while the energization strategies are described as involving DC pulses, embodiments may use variations and remain within the spirit and scope of the disclosure. For example, exponentially-decaying pulses, exponentially-increasing pulses, and combinations may be used. Further, in some embodiments, high-frequency alternating pulses may also be used.

It should be understood that the mechanism of cell destruction in electroporation is not primarily due to heating effects, but rather to cell membrane disruption through application of a high-voltage electric field. Thus, electroporation may avoid some possible thermal effects that may occur when using radio frequency (RF) energy. This "cold therapy" thus has desirable characteristics.

With this background, and now referring again to FIG. 1, system 10 includes a catheter electrode assembly 12 including at least one catheter electrode configured to be used as briefly outlined above and as described in greater detail below. Electrode assembly 12 is incorporated as part of a medical device such as a catheter 14 for electroporation therapy of tissue 16 in a body 17 of a patient. In the illustrative embodiment, tissue 16 comprises heart or cardiac tissue. It should be understood, however, that embodiments may be used to conduct electroporation therapy with respect to a variety of other body tissues.

FIG. 1 further shows a plurality of return electrodes designated 18, 20, and 21, which are diagrammatic of the body connections that may be used by the various sub-systems included in the overall system 10, such as an electroporation generator 26, an electrophysiology (EP) monitor such as an ECG monitor 28, a localization and navigation system 30 for visualization, mapping and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode. In other embodiments, return electrodes 18, 20, and 21 may be any other type of electrode suitable for use as a return electrode including, for example, one or more catheter electrodes. Return electrodes that are catheter electrode may be part of electrode assembly 12 or part of a separate catheter (not shown). System 10 may further include a main computer system 32 (including an electronic control unit 50 and data storage-memory 52), which may be integrated with system 30 in certain embodiments. System 32 may further include conventional interface components, such as various user input/output mechanisms 34A and a display 34B, among other components.

Electroporation generator 26 is configured to energize the electrode element(s) in accordance with an electroporation energization scheme, which may be predetermined or may be user-selectable. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude must be increased to achieve electroporation.

Electroporation generator 26, sometimes also referred to herein as a DC energy source, is a monophasic electroporation generator 26 configured to generate a series DC energy pulses that all produce current in the same direction. In other embodiments, electroporation generator is biphasic or polyphasic electroporation generator configured to produce DC energy pulses that do not all produce current in the same direction. In some embodiments, electroporation generator 26 is a monophasic defibrillator. The defibrillator is configured to output energy in DC pulses at selectable energy levels, such as fifty joules, one hundred joules, two hundred joules, and the like. Other embodiments may have more or fewer energy settings and the values of the available setting may be the same or different. For successful electroporation, some embodiments utilize the two hundred joule output level. Electroporation generator 26 may output a DC pulse having a peak magnitude of about between about negative one kilovolt (kV) and about negative two kV at the two hundred joule output level. In some embodiments, electroporation generator 26 outputs a DC pulse having a peak magnitude of about between about negative 1.5 kV and about negative 2.0 kV. Other embodiments may output any other suitable voltage, including a positive voltage. In some embodiments, the monophasic defibrillator is a Lifepak 9 defibrillator available from Physio-Control, Inc., of Redmond, Washington, USA.

A variable impedance device 27 allows the impedance of the system to be varied to limit arcing from the catheter electrode of catheter 14. Moreover, variable impedance device 27 may be used to change one or more characteristics, such as amplitude, duration, pulse shape, and the like, of an output of electroporation generator 26. Although illustrated as a separate component, variable impedance device 27 may be incorporated in catheter 14 or generator 26. Further, although illustrated as being coupled between catheter 14 and generator 26, in some embodiments, variable impedance device 27 may be located in other positions (e.g., coupled between a skin plate and generator 26).

Variable impedance device 27 includes one or more impedance elements, such as resistors, capacitors, or inductors (not shown) connected in series, parallel, or combinations of series and/or parallel. In the illustrated embodiment, variable impedance device 27 is connected in series with catheter 14. Alternatively, the impedance elements of variable impedance device 27 may be connected in parallel with catheter 14 or in a combination of series and parallel with catheter 14. Moreover, in other embodiments, the impedance elements of variable impedance device 27 are connected in series and/or parallel with return electrode 18. Some embodiments include more than one variable impedance device 27, each of which may include one or more impedance elements. In such embodiments, each variable impedance device 27 may be connected to a different catheter electrode or group of catheter electrodes to allow the impedance through each catheter electrode or group of catheter electrodes to be separately varied.

In the illustrative embodiment, the variable impedance is a variable resistance. In some embodiments variable impedance device 27 includes one or more resistors (not shown) removably connected between generator 26 and catheter 14. The resistors may be connected in series, parallel, or any combination of series and parallel connections to produce a desired system impedance. Some or all of the resistors may be added, removed, or connected differently to vary the system impedance. In some other embodiments, variable impedance device 27 is variable resistor, such as a rheostat or a potentiometer. In still other embodiments, variable impedance device 27 includes resistors coupled together by one or more switches to allow the resistors to be selectively switched in and out of the connection between generator 26 and catheter 14. Such a variable impedance device 27 may also be configured to allow some or all of the resistors to be selectively connected together in series or in parallel with each other. In some embodiments, variable impedance device 27 is variable in response to an appropriate control signal from computer system 32. The resistors may be any suitable type of resistor. In all embodiments, the resistors (or other impedance elements) have relatively high energy ratings sufficient to handle the output of generator 26 without being damaged. In some embodiments, variable impedance device 27 includes Ohmite PulsEater resistors available from Ohmite Mfg. Co. of Warrenville, IL, USA. With continued reference to FIG. 1, as noted above, catheter 14 may comprise functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal end 48. Catheter 14 may also include other conventional components not illustrated herein such as a temperature sensor, additional electrodes, and corresponding conductors or leads. The connector 40 provides mechanical and electrical connection(s) for cable 56 extending from generator 26. The connector 40 may comprise conventional components known in the art and as shown is disposed at the proximal end of catheter 14.

Handle 42 provides a location for the clinician to hold catheter 14 and may further provide means for steering or the guiding shaft 44 within body 17. For example, handle 42 may include means to change the length of a guidewire extending through catheter 14 to distal end 48 of shaft 44 or means to steer shaft 44. Moreover, in some embodiments, handle 42 may be configured to vary the shape, size, and/or orientation of a portion of the catheter. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced/retracted and/or steered or guided through body 17 to a desired location such as the site of tissue 16, including through the use of guidewires or other means known in the art.

In some embodiments, catheter 14 is a hoop catheter having catheter electrodes (not shown) distributed about one or more hoops at the distal end of shaft 44. The diameter of the hoop(s) may be variable. In some embodiments, the hoop catheter has a maximum diameter of about twenty-seven millimeters (mm). In some embodiments, the hoop diameter is variable between about fifteen mm and about twenty eight mm. Alternatively, the catheter may be a fixed diameter hoop catheter or may be variable between different diameters. In some embodiments, catheter 14 has fourteen catheter electrodes. In other embodiments, catheter 14 includes ten catheter electrodes, twenty catheter electrodes, or any other suitable number of electrodes for performing electroporation. In some embodiments, the catheter electrodes are ring electrodes, such as platinum ring electrodes. Alternatively, the catheter electrodes may be any other suitable type of electrodes, such as single sided electrode or electrodes printed on a flex material. In various embodiments, the catheter electrodes have lengths of 1.0 mm, 2.0 mm, 2.5 mm, and/or any other suitable length for electroporation.

FIGS. 2 and 3 show the distal end of an example variable diameter hoop catheter 200 usable as catheter 14. Hoop catheter 200 includes fourteen catheter electrodes 202. Catheter electrodes 202 are ring electrodes. In FIG. 2, hoop catheter 200 is shown in its fully expanded configuration with a diameter 204 of about 24 mm. In FIG. 3, hoop catheter 200 is shown in its fully contracted configuration with a diameter of about 15 mm. In other embodiments, catheter 200 may be variable between different diameters and/or may include any other suitable number of electrodes for performing electroporation.

The localization and navigation system 30 may be provided for visualization, mapping and navigation of internal body structures. System 30 may comprise conventional apparatus known generally in the art (e.g., an EnSite NAVX™ Navigation and Visualization System, commercially available from Abbott Laboratories. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system.

As described herein, electroporation through catheter, such as a hoop catheter used in cardiac ablation procedures, can creates arcs. These arcs create shockwaves that may cause barotrauma (i.e., pressure wave damage to tissue) and/or generate larger air bubbles that those generated during non-arcing shocks. Accordingly, the systems and methods described above are directed to limiting or preventing such arcing.

Several factors may influence the formation of electrical arcs from catheter electrodes in an electroporation system, such as system 10. In general, the various factors combine to define in a maximum energy that can be delivered by an electroporation generator to a catheter in a single pulse without causing arcing from the catheter. The total electrode surface area is a strong determinant of the maximum allowable energy which can be safely delivered in a single pulse without arcing from the catheter electrode(s). The total electrode surface area is the sum of all individual electrode surface areas. The catheter shape is another determinant of the maximum allowable pulse energy. For example when a catheter hoop is deployed in the minimum possible diameter, the threshold for arcing is lower than when the hoop is deployed in the maximum diameter. The time between individual energy applications is another determinant of the maximum allowable pulse energy. For example when one pulse is "followed quickly" by a second pulse, the arc threshold on the second pulse is lower than the threshold for the first pulse, because some of the gas bubbles which were created on the electrode by the first pulse are still present when the second pulse is applied. The formation of the insulating gas layer on the electrode is cumulative, and if/when the layer forms a complete insulator an arc can occur. This effect has been observed in pulses applied about 30 seconds apart (i.e. it is not only a short-duration phenomenon).

Figure 4:
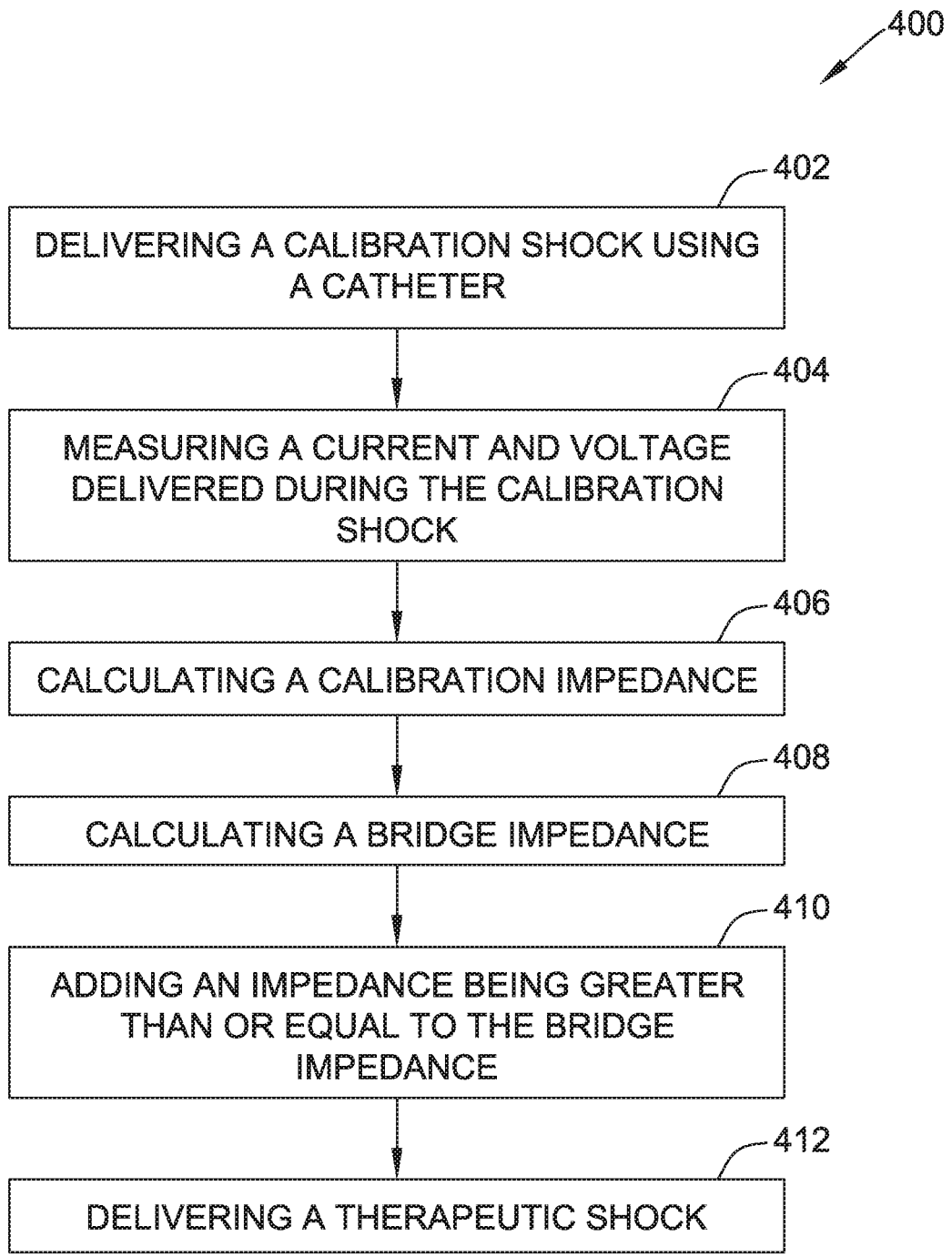
FIG. 4 is a flowchart of a method for limiting arcing during an electroporation procedure that may be used with the system shown in FIG. 1.

FIG. 4 is a flowchart of a method 400 for limiting arcing during an electroporation procedure. Method 400 may be implemented, for example, using system 10 (shown in FIG. 1). Although method 400 will be described with reference to system 10, it should be understood that method 400 may be performed using any suitable electroporation system.

Method 400 includes delivering 402 a calibration shock using a catheter, such as catheter 14 (shown in FIG. 1). In the exemplary embodiment, calibration shock is a fifty joule shock or a hundred joule shock. Alternatively, calibration shock may have any energy that enables performing method 400. Notably, because of the lower energy level, fifty joule and hundred joule shocks delivered using catheter 14 generally never result in arcing.

Method 400 further includes measuring 404 a current delivered during the calibration shock and a voltage delivered during the calibration shock. The delivered current and voltage may be measured, for example, using ECG monitor 28 (shown in FIG. 1). Based on the delivered current and voltage, an impedance of the calibration shock is calculated 406 (e.g., by computer system 32 (shown in FIG. 1)). In some embodiments, the "calibration shock" impedance may be calculated without actually delivering 402 a calibration shock. That is, the impedance may be measured with an Ohm-meter or other suitable device.

Notably, the impedance for the calibration shock will vary based on the hoop size of the catheter. For example, in one experiment, the measured impedance for a 27 mm diameter hoop catheter was 66.4 Ohms, while the measured impedance for a 16 mm diameter catheter was 72.1 Ohms. Accordingly, the hoop catheter should be set at a largest possible diameter when the calibration shock is delivered (or at least at the same diameter that will be used for the subsequent therapeutic shock). Alternatively, the hoop catheter may be set at a different diameter for the calibration shock, but the measured "calibration shock" impedance should be adjusted based on the actual hoop size to be used for the subsequent therapeutic shock.

Subsequently, a bridge impedance is calculated 408 (e.g., by computer system 32) based on the calibration shock impedance and a target impedance. Specifically, the target impedance is a predetermined total impedance value selected to prevent arcing. That is, if a two hundred joule shock is delivered with the target impedance, no arcing should occur. The bridge impedance is the additional impedance needed (beyond the calibration shock impedance) to reach the target impedance. Accordingly, the bridge impedance is calculated 408 as the difference between the target impedance and the calibration shock impedance.

Once the bridge impedance is calculated 408, to prevent arcing, an impedance being greater than or equal to the bridge impedance is added 410 in series with the catheter. Generally, the impedance is not substantially greater than the bridge impedance, as too much impedance can reduce therapeutic effects. The impedance may be added 410, for example, using variable impedance device 27 (shown in FIG. 1) and/or by connecting an external resistor in series with the catheter. In some embodiments, computer system 32 calculates 408 bridge impedance 408 and automatically instructs variable impedance device 27 to add the impedance (i.e., without requiring user input). Alternatively, computer system 32 may cause a value of the bridge impedance to be displayed (e.g., on display 34B), so that a user can determine the bridge impedance and modify the system to add the appropriate impedance.

In some embodiments, instead of adding 410 an impedance (which reduces the total amount of energy delivered by a subsequent therapeutic shock), the total therapeutic shock energy is modified by adding or removing one or more capacitors in the system. For example, the shocks described herein are generally delivered by charging and subsequently discharging a relatively large capacitor (e.g., a 10 micro Farad (μF) capacitor) in series with the catheter. If that capacitor is replaced by multiple capacitors that are equivalent (e.g., ten 1 μF capacitors coupled in parallel), the total therapeutic shock energy can be modified by modifying the number of capacitors (e.g., adding or removing one or more capacitors as needed using, for example, a switching device). This is because modifying the number of capacitors changes the capacitance, which in turn affects the total delivered energy (i.e., $E=0.5*C*V^2$). Specifically, when using a smaller capacitance, the charging voltage and initial current will remain the same, but discharging will be faster, resulting in voltage and current decreasing faster during the shock, and resulting in a reduced total therapeutic shock energy.

In other embodiments, instead of modifying the capacitance in series with the catheter, a charging voltage for the capacitance in series with the catheter may be modified for the subsequent therapeutic shock. For example, based on the calibration shock, the capacitance may be charged to 2100 Volts instead of 2300 Volts.

After the impedance is added 410, a therapeutic shock (e.g., a two hundred joule shock) is delivered 412. With the impedance added 410 in series with the catheter, the resulting total impedance during any subsequent shocks should be greater than or equal to the target impedance. Accordingly, delivering 412 the therapeutic shock with the impedance in series with the catheter should not result in any arcing.

In one embodiment, the calibration shock and the therapeutic shock are delivered at the same anatomical location. That is, the calibration shock is delivered at the same site that the ablation is to be performed at (e.g., a pulmonary vein antrum). Alternatively, in some embodiments, the calibration shock is delivered at a different location than the therapeutic shock. For example, the calibration shock may be delivered in a pulmonary vein ostium and/or a blood pool.

Shocks delivered in a blood pool will generally have a lower measured impedance than shocks delivered at other locations. Accordingly, if a calibration shock impedance is measured from a shock delivered in a blood pool, the resulting calculated bridge impedance will generally be larger (as there will be a greater difference between the calibration shock impedance and the target impedance). This provides an extra impedance buffer during the therapeutic shock, as the total impedance for the therapeutic shock will be the sum of the "baseline" impedance for the ablation site (i.e., the impedance without the added impedance, which will be generally higher than the blood pool calibration impedance) and the impedance corresponding to the bridge impedance. That is, in such an embodiment, the total impedance for the therapeutic shock will generally be higher than the target impedance.

Figure 5:
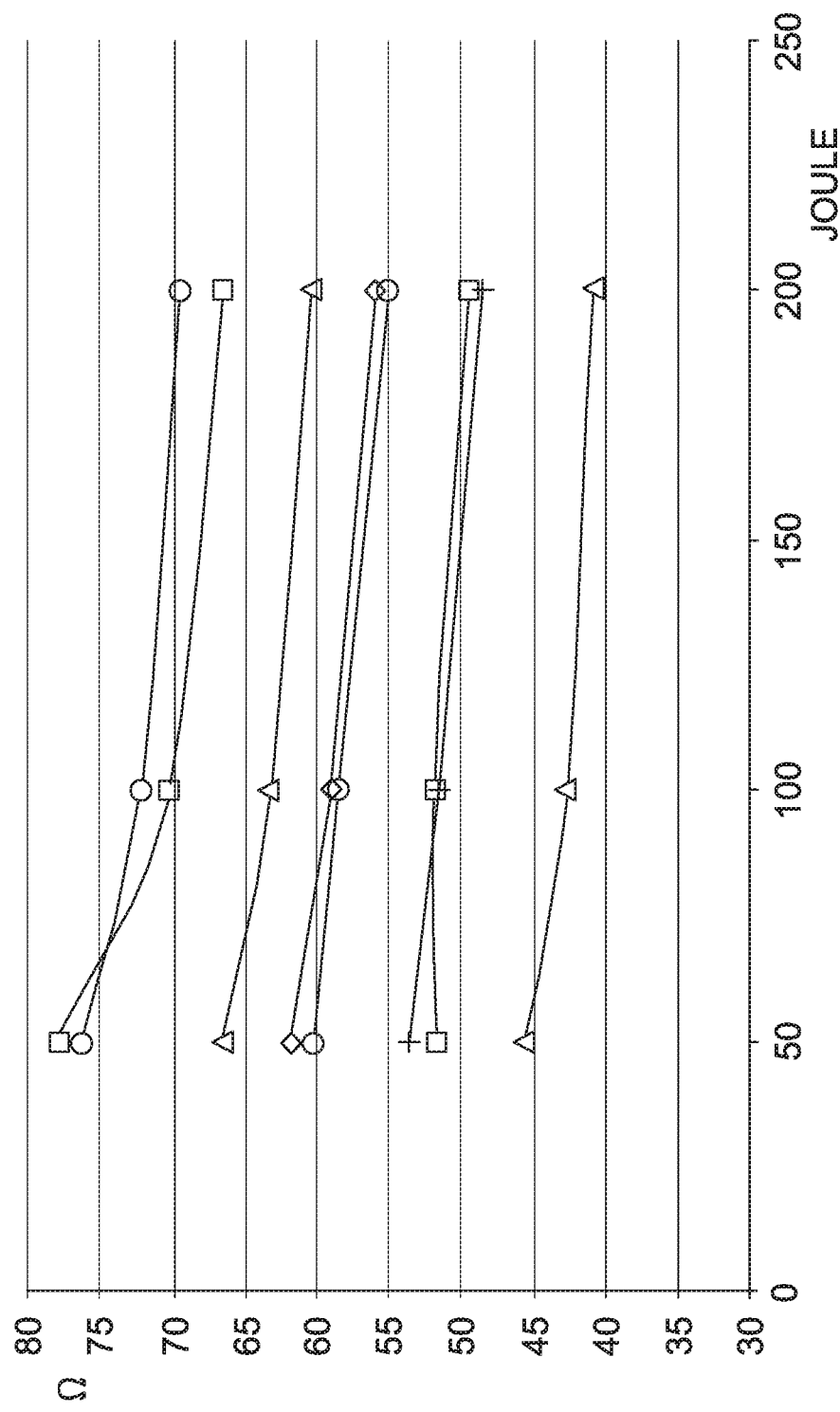
FIG. 5 is a graph showing experimental results of impedance values for fifty, one hundred, and two hundred joule shocks in multiple different subjects.

Method 400 is effective because the impedance value for a shock delivered to a subject does not substantially vary at different shock energies. That is, the impedance value for a fifty or one hundred joule shock in a subject will be substantially similar to the impedance value for a two hundred joule shock. For example, FIG. 5 is a graph 500 showing experimental results of impedance values for fifty, one hundred, and two hundred joule shocks in multiple different subjects. As shown in FIG. 5, although the impedance values varied from subject to subject (i.e., from approximately 77 ohms to approximately 40 ohms), the impedance values for a given subject were substantially similar at different energy levels (i.e., within 5 ohms).

Figure 6:
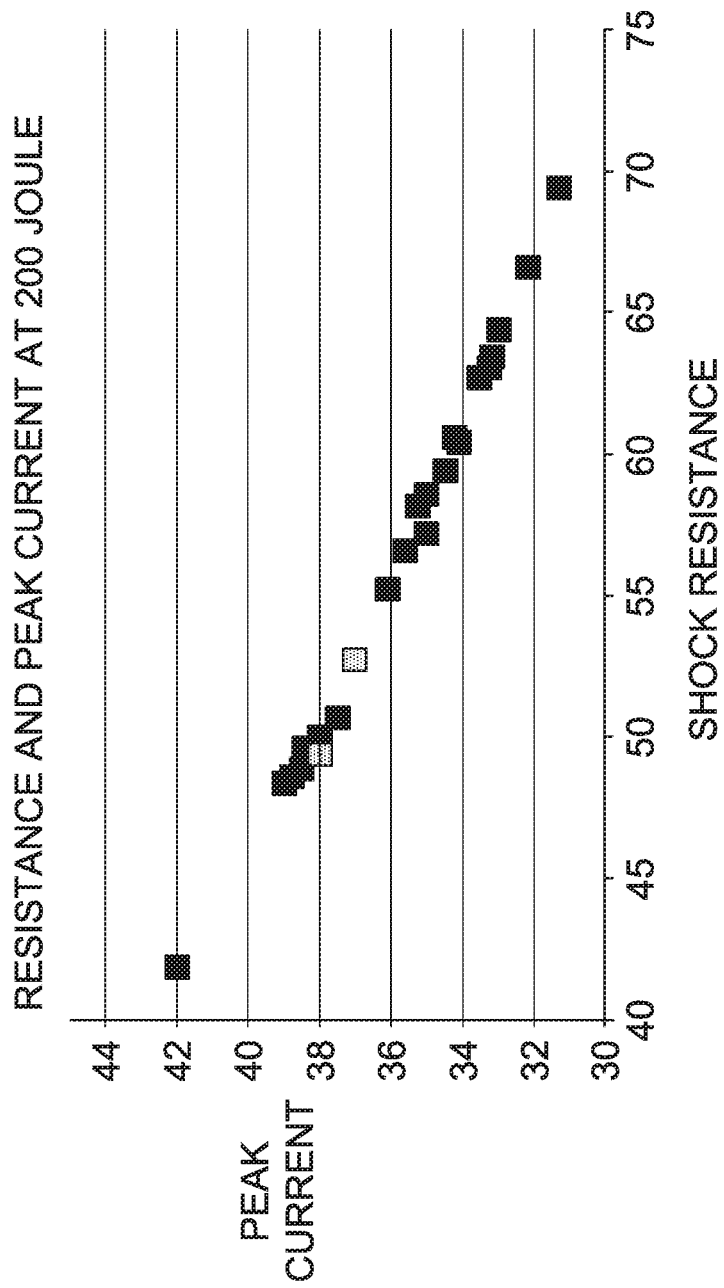
FIG. 6 is a graph showing experimental results of resistances and peak currents recorded for two hundred joule shocks.

In one embodiment, the target impedance is approximately 55 ohms. For example, FIG. 6 is a graph 600 showing experimental results of resistances and peak currents recorded for two hundred joule shocks. In graph 600, solid squares indicate that no arcing occurred, and the two hatched squares indicate arcing occurred. As shown in FIG. 6, in these experimental results, no arcing occurred at impedances at or above 55 ohms. Accordingly, 55 ohms is a suitable target impedance.

In other embodiments, the target impedance may be greater than approximately 55 ohms. For example, the target impedance may be in a range from approximately 55 ohms to approximately 70 ohms (e.g., approximately 55 ohms, approximately 60 ohms, approximately 65 ohms, or approximately 70 ohms). Using a higher target impedance reduces the likelihood that arcing will occur during the therapeutic shock. For example, FIG. 5 shows that impedance values for the same subject will be (slightly) lower at higher energies. Further, as described above, when multiple therapeutic pulses are delivered within a short period of time, the arc threshold for a subsequent pulse may be lower than the arc threshold for the initial pulse, because gas bubbles created by the initial pulse are still present when the subsequent pulse is applied. Accordingly, using a higher target impedance reduces the likelihood that arcing will occur when multiple therapeutic pulses are delivered.

Further, method 400 is effective because shocks delivered at different locations in a subject will be not be substantially different from one another (although shocks delivered in blood pools will generally be slightly lower, as described above). For example, the following Table 1 shows experimental results of average impedance and standard deviation of impedance for a plurality of shocks delivered at different locations for a plurality of animals. That is, for each animal, shocks were delivered at different locations within that animal, and the results were recorded.

| animal | Average of Patient Impedance (Ω) | Standard Deviation Of Patient Impedance (Ω) | # of shocks |
| --- | --- | --- | --- |
| 16p0483 | 55 | 3 | 3 |
| 16p0484 | 75 | 6 | 2 |
| 16p0485 | 60 | 3 | 4 |
| 16p0487 | 64 | 7 | 3 |
| 16p0489 | 52 | 5 | 3 |
| 16p0490 | 58 | 4 | 2 |
| 16p0491 | 61 | 1 | 3 |
| 16p0492 | 55 | 3 | 3 |
| 16p0494 | 63 | 3 | 2 |

As demonstrated by Table 1, the variation (i.e., the standard deviation) in impedance between different locations is relatively low.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method for limiting arcing during an electroporation procedure, the method comprising:
   delivering a calibration shock using a catheter;
   measuring a current delivered during the calibration shock and a voltage delivered during the calibration shock;
   calculating, using a processing device, a calibration shock impedance based on the current delivered and the voltage delivered;
   calculating, using the processing device, a bridge impedance based on the calibration shock impedance and a target impedance, wherein the bridge impedance is a difference between the calibration shock impedance and the target impedance;
   adding, in response to the calculation of the bridge impedance, an impedance in series with the catheter, the impedance added based on the calculated bridge impedance and being greater than or equal to the bridge impedance; and
   delivering a therapeutic shock including a therapeutic electrical pulse using the catheter in series with the added impedance, wherein the calibration shock includes a calibration electrical pulse with an energy level i) selected to ensure no arcing occurs during delivery of the calibration shock and ii) lower than an energy level of the therapeutic electrical pulse.

2. The method of claim 1, wherein delivering the calibration shock comprises delivering one of a fifty joule calibration shock and a one hundred joule calibration shock.

3. The method of claim 1, wherein delivering the therapeutic shock comprises delivering a two hundred joule therapeutic shock.

4. The method of claim 1, wherein delivering the calibration shock comprises delivering the calibration shock at an anatomical site, and wherein delivering the therapeutic shock comprises delivering the therapeutic shock at a same anatomical site as the anatomical site that the calibration shock was delivered to.

5. The method of claim 1, wherein delivering the calibration shock comprises delivering the calibration shock at a first anatomical site, and wherein delivering the therapeutic shock comprises delivering the therapeutic shock at a second anatomical site different than the first anatomical site.

6. The method of claim 5, wherein the first anatomical site is a blood pool.

7. The method of claim 1, wherein adding the impedance comprises adding a resistor in series with the catheter.

8. The method of claim 1, wherein adding the impedance comprises automatically adding the impedance, using the processing device, by controlling a variable impedance device.

9. A system for limiting arcing during an electroporation procedure, the system comprising:
- a catheter configured to deliver a calibration shock and a therapeutic shock; and
- a processing device communicatively coupled to the catheter, the processing device configured to:
  - calculate, based on a measured current delivered during the calibration shock and a measured voltage delivered during the calibration shock, a calibration shock impedance;
  - calculate a bridge impedance based on the calibration shock impedance and a target impedance, wherein the bridge impedance is a difference between the calibration shock impedance and the target impedance; and
  - add, in response to the calculation of the bridge impedance, prior to delivery of the therapeutic shock including a therapeutic electrical pulse, an impedance in series with the catheter, the impedance added based on the calculated bridge impedance and being greater than or equal to the bridge impedance, wherein the calibration shock includes a calibration electrical pulse with an energy level i) selected to ensure no arcing occurs during delivery of the calibration shock and ii) lower than an energy level of the therapeutic electrical pulse.

10. The system of claim 9, wherein the calibration shock is one of a fifty joule calibration shock and a one hundred joule calibration shock.

11. The system of claim 9, wherein the therapeutic shock is a two hundred joule therapeutic shock.

12. The system of claim 9, wherein the catheter is configured to deliver the calibration shock at an anatomical site, and configured to deliver the therapeutic shock at the anatomical site.

13. The system of claim 9, wherein the catheter is configured to deliver the calibration shock at a first anatomical site, and configured to deliver the therapeutic shock at a second anatomical site different than the first anatomical site.

14. The system of claim 13, wherein the first anatomical site is a blood pool.

15. The system of claim 9, wherein the target impedance is in a range from fifty five ohms to seventy ohms.

16. The system of claim 9, wherein the system further comprises a variable impedance device, and wherein to add the impedance in series with the catheter, the processing device is configured to automatically add the impedance in series with the catheter by controlling the variable impedance device.

* * * * *